(12) United States Patent
DeLuca et al.

(10) Patent No.: US 7,559,921 B2
(45) Date of Patent: Jul. 14, 2009

(54) DEVICE FOR REMOVING A LODGED MASS

(76) Inventors: James T. DeLuca, 375 Post Ave., Westbury, NY (US) 11590; Paul V. DeLuca, 50 Circle Dr., Plandome Manor, NY (US) 11030

( * ) Notice: Subject to any disclaimer, the term of this patent is extended or adjusted under 35 U.S.C. 154(b) by 242 days.

(21) Appl. No.: 11/256,446

(22) Filed: Oct. 24, 2005

(65) Prior Publication Data

US 2006/0161170 A1 Jul. 20, 2006

Related U.S. Application Data

(60) Provisional application No. 60/644,833, filed on Jan. 19, 2005.

(51) Int. Cl.
*A61M 1/00* (2006.01)
(52) U.S. Cl. ............... 604/317; 604/1; 604/2; 604/3; 604/18; 604/289; 604/416; 604/540
(58) Field of Classification Search ............ 604/1, 604/2, 3, 18, 289, 317, 416, 540
See application file for complete search history.

(56) References Cited

U.S. PATENT DOCUMENTS

| | | | | |
|---|---|---|---|---|
| 3,499,393 A | * | 3/1970 | Bent | 604/149 |
| 3,628,532 A | * | 12/1971 | Magrath | 128/204.17 |
| 3,665,919 A | * | 5/1972 | Laerdal | 604/149 |
| 3,939,830 A | * | 2/1976 | da Costa | 128/205.18 |
| 4,300,550 A | * | 11/1981 | Gandi et al. | 128/207.18 |
| 5,562,918 A | * | 10/1996 | Stimpson | 424/451 |
| 7,048,724 B2 | * | 5/2006 | Grossman et al. | 604/319 |

OTHER PUBLICATIONS

Thesaurus.com.*

* cited by examiner

*Primary Examiner*—Michele Kidwell
*Assistant Examiner*—Ilya Y Treyger
(74) *Attorney, Agent, or Firm*—Charles E. Temko

(57) ABSTRACT

A vacuum device for removing a lodged mass or bolus from the throat of a choking victim. The device includes a pump for creating a vacuum chamber communicating with a mouthpiece having a frangible membrane. A resilient striker fractures the membrane to generate a substantially instantaneous vacuum to the mouthpiece to dislodge the mass. In one embodiment, the membrane is substituted by a manually displaceable sealing member, which is resealed after use of the device by movement of a vacuum-generating plunger.

3 Claims, 4 Drawing Sheets

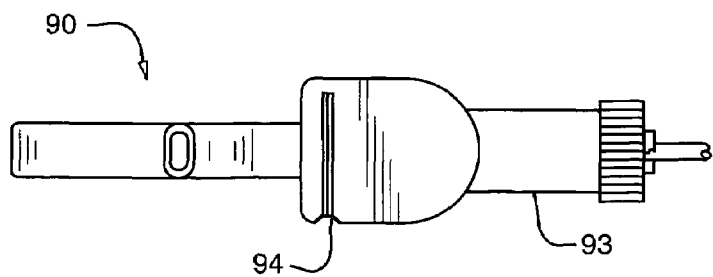
FIG. 5
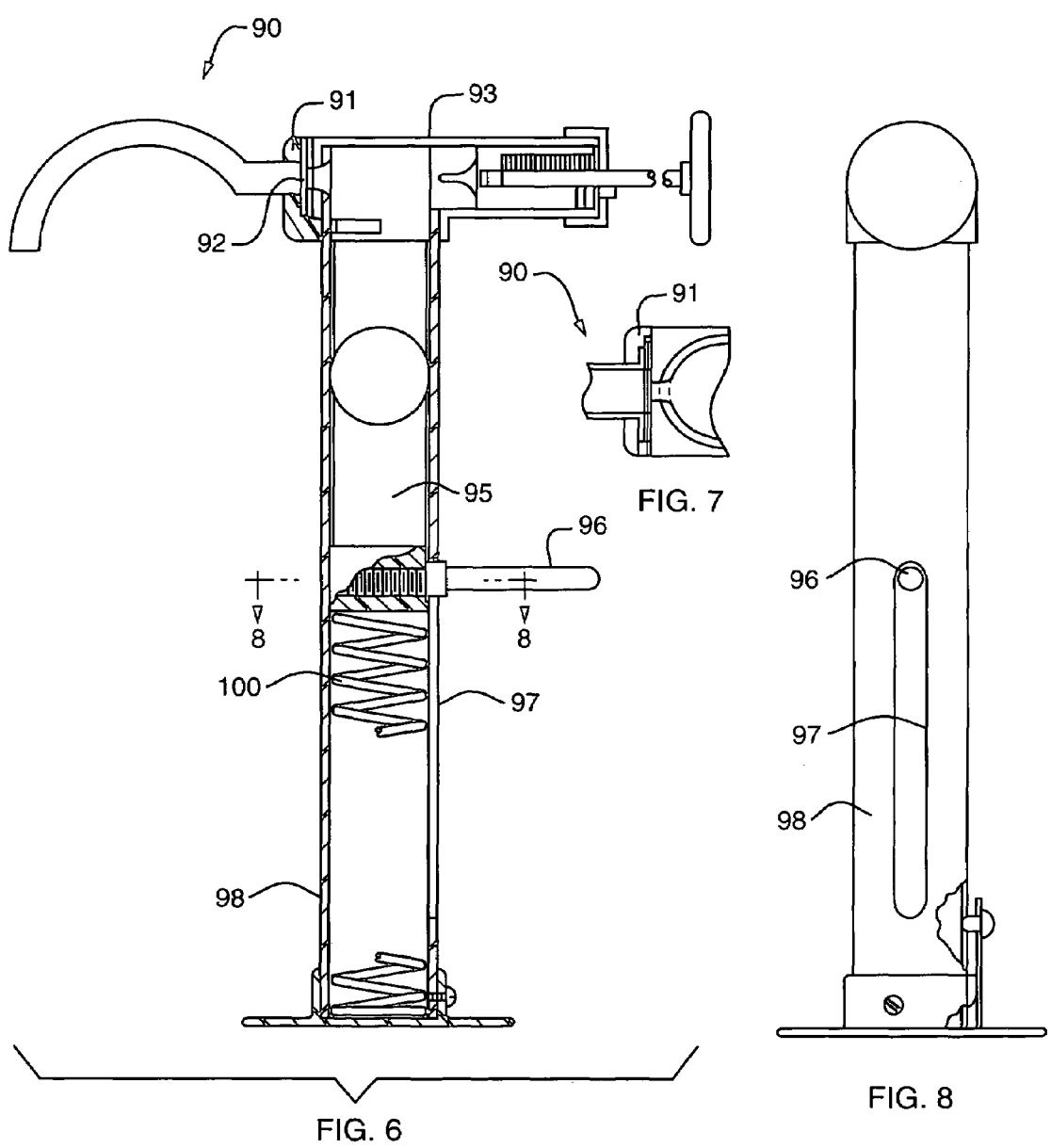
FIG. 7
FIG. 6
FIG. 8

DEVICE FOR REMOVING A LODGED MASS

RELATED APPLICATION

Reference is made to our copending provisional application, Ser. No. 60/644,833; filed Jan. 19, 2005, to which a claim of priority is made.

BACKGROUND OF THE INVENTION

This invention relates to anti-choke devices employed for removing a mass or bolus lodged in the throat of a victim, and more particularly, to a device which is capable of improved operation, which may be produced at relatively modest cost.

As disclosed in U.S. Patent to Litkouhi, et. al., U.S. Pat. No. 6,478,770, when a vacuum pressure is released after positioning a mouthpiece in the throat of a victim, it is desirable that the pressure be created substantially instantaneously, rather than built up gradually by a vacuum pump. As disclosed in that patent, the pressure is provided by a sealed vacuum canister having a penetrable membrane to provide instant vacuum pressure. While this construction is not without utility, it is to be appreciated that with passage of time in storage, the canister will lose vacuum pressure so that unless periodically serviced, the system may be inoperable when it is required.

It is known in the art to provide vacuum pump devices which build up vacuum pressure gradually, as a result of which they do not provide the instantaneous vacuum surge to the mouthpiece for maximum effect.

SUMMARY OF THE INVENTION

Briefly stated, the invention conLemplates the provision of an improved device of the type described in which the above-mentioned disadvantage has been eliminated. To this end, the device includes a cylindrical tube having a spring-loaded striker at one end thereof, and means for engaging an end of the mouthpiece tube in substantially leak-proof relation, which includes a frangible membrane. Extending laterally from the tube is a small hand pump having a lockable plunger, which creates a vacuum with a single outward stroke. When the mouthpiece is positioned, a manually operated means releases the striker which penetrates the membrane to release the vacuum pressure instantaneously to the engaged end of the mouthpiece. The process may be repeated if necessary, using a replacement mouthpiece. In one embodiment, the membrane is replaced by a selectively displaced seal which is repositioned for a second use by movement of the plunger.

BRIEF DESCRIPTION OF THE DRAWINGS

In the drawings, to which reference will be made in the specification, similar reference characters have been employed to designate corresponding parts throughout the several views.

FIG. 5 is a top plan view of a fourth embodiment.

FIG. 6 is a central sectional view of the fourth embodiment.

FIG. 7 is an elevational view as seen from the right-hand portion of FIG. 6.

FIG. 8 is an enlarged fragmentary sectional view corresponding to the upper left-hand portion of FIG. 6.

DETAILED DESCRIPTION OF THE DISCLOSED EMBODIMENTS

Figure 1:
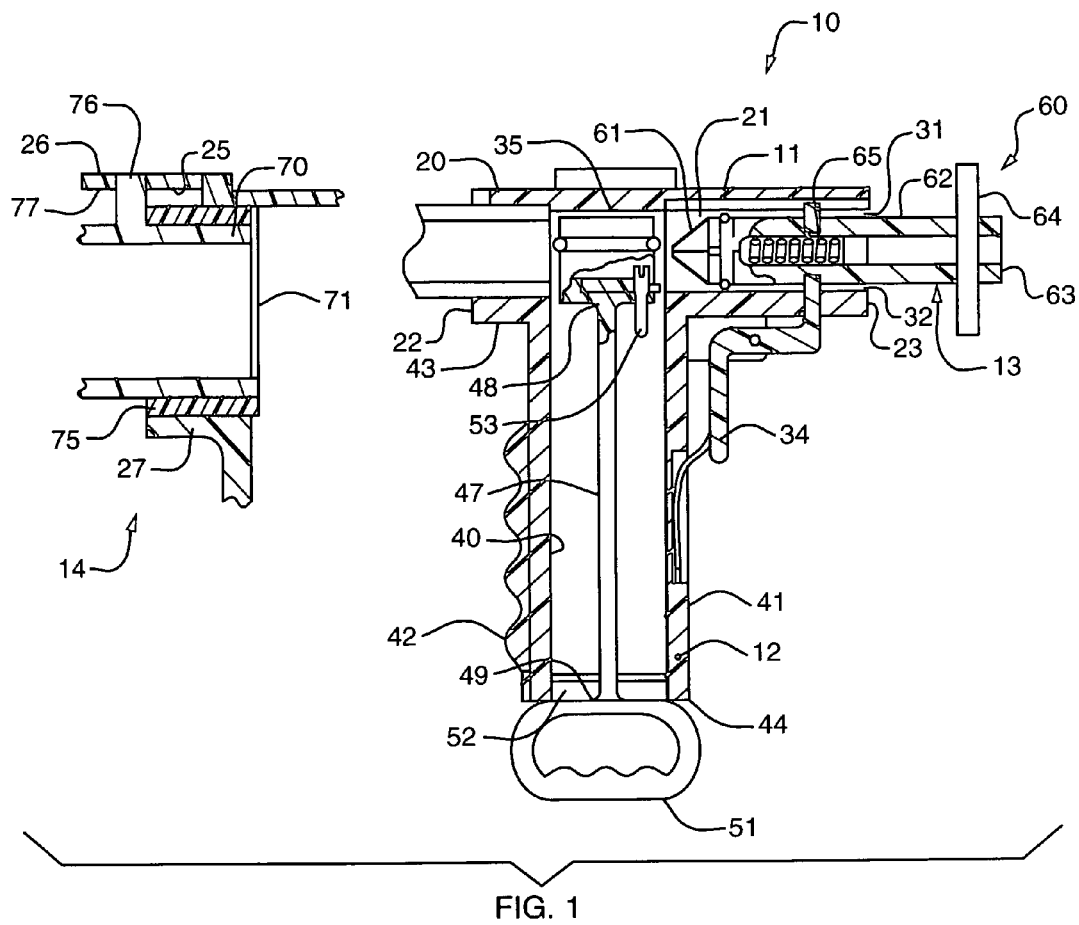
FIG. 1 is a fragmentary schematic sectional view of an embodiment of the invention.
Figure 2:
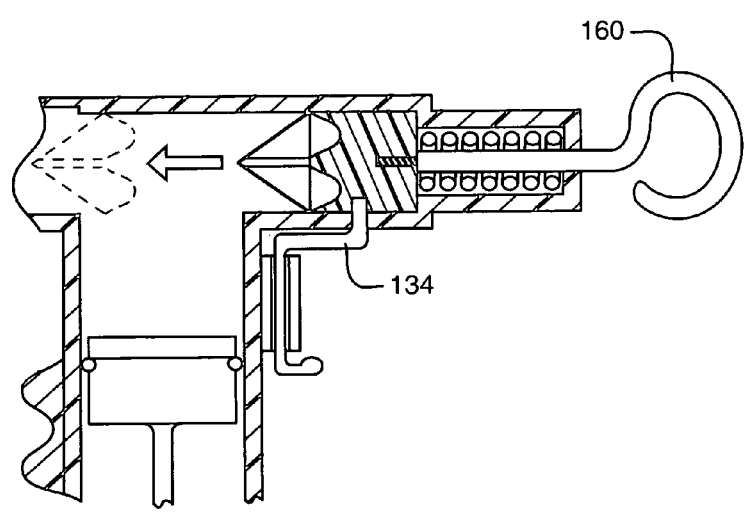
FIG. 2 is a fragmentary schematic sectional view of a second embodiment of the invention.

In accordance with the first embodiment of the invention, the device, generally indicated by reference character 10, comprises an elongated tube element 11, a laterally-extending pump element 12, a striker element 13, and a mouthpiece element 14. It is contemplated that most of the elements can be formed by injection molding techniques of synthetic resinous material known in the art.

The tube element 11 is bounded by an outer surface 20, an inner surface 21, as well as first and second ends 22 and 23, respectively. The first end 22 forms a socket 25 for receiving an outer end of the mouthpiece element 14, which is provided with a slot 26 and a resilient sealing liner 27. The second end 23 forms first and second openings 31-32 for supporting the striker element 13, and forms an opening for a manually-operated trigger 34. An intermediate section 35 communicates with the pump element 12.

The pump element 12 is formed to include a hollow cylinder 40, having an outer surface 41, including a grip portion 42, and extends from a connecting end 43 to a free end 44, which includes a recess for the pivotally-mounted trigger 34. A vacuum plunger 47 extends from an inner end 48 to an outer end 49 having a manually engageable handle 51. A recess 52 selectively engages a latch 53 to maintain the plunger 47 in extended condition, thus creating a vacuum within the device.

The striker element 13 extends from a manually-engageable terminal 60 to a penetrating nose 61. A longitudinal body 62 is provided at its outer end 63 with a cocking member 64. A spring 65 urges the striker element leftwardly, as seen in FIG. 1, when released by the trigger 34.

The mouthpiece element 14 may be of conventional configuration, including an engagement sleeve 70 closed by a membrane 71 held in position by a collar 75. A laterally-extending projection 76 engages a corresponding slot 77 at the time of interconnection in substantially leak-proof relation. Use of the device contemplates the discarding of the mouthpiece element with each use, thus providing a fresh membrane 71 prior to the commencement of operation.

Operation

The device is normally stored in the condition illustrated in the drawing until needed.

Upon the occurrence of an emergency, the device is used by first cocking the striker element, which is engaged by the manually operable trigger, following which the pump plunger is moved laterally outwardly to create a vacuum. When the plunger has reached its outward excursion, it is latched in position by the latch 53.

The mouthpiece element is then inserted into the mouth of the victim and positioned in known manner, following which the trigger is pulled to release the striker element which moves inwardly to puncture the foil membrane 71, thus communicating the vacuum pressure to the mouthpiece element in a substantially instantaneous manner. Should a second application become necessary, the operation is repeated using a replacement mouthpiece element.

Upon completion of the above operation, the mouthpiece element is removed from the victim, and disconnected from the remainder of the device to be discarded. It is replaced by another mouthpiece element, including a new membrane seal.

As compared with prior art devices employing a vacuum pump, all of the required pressure is created with a single pump stroke immediately before use, rather than building up vacuum with repeated pump strokes, and the vacuum pressure created in the disclosed device need be maintained for only a relatively short period of time.

Turning now to the second embodiment of the invention, to avoid needless repetition, parts corresponding to those of the first embodiment have been designated by similar reference characters with the additional prefix "1".

The second embodiment differs from the first embodiment principally in simplification of manufacture, to reduce cost of production. The pivotally-mounted trigger is replaced by a sliding molded trigger. The outward part of the striker element may be formed from bent wire and threadedly engaged with the inner portion of the striker element which may be of molded configuration. The nose portion of the striker element includes axially aligned grooves to facilitate air flow from the mouthpiece element.

Figures 3, 4:
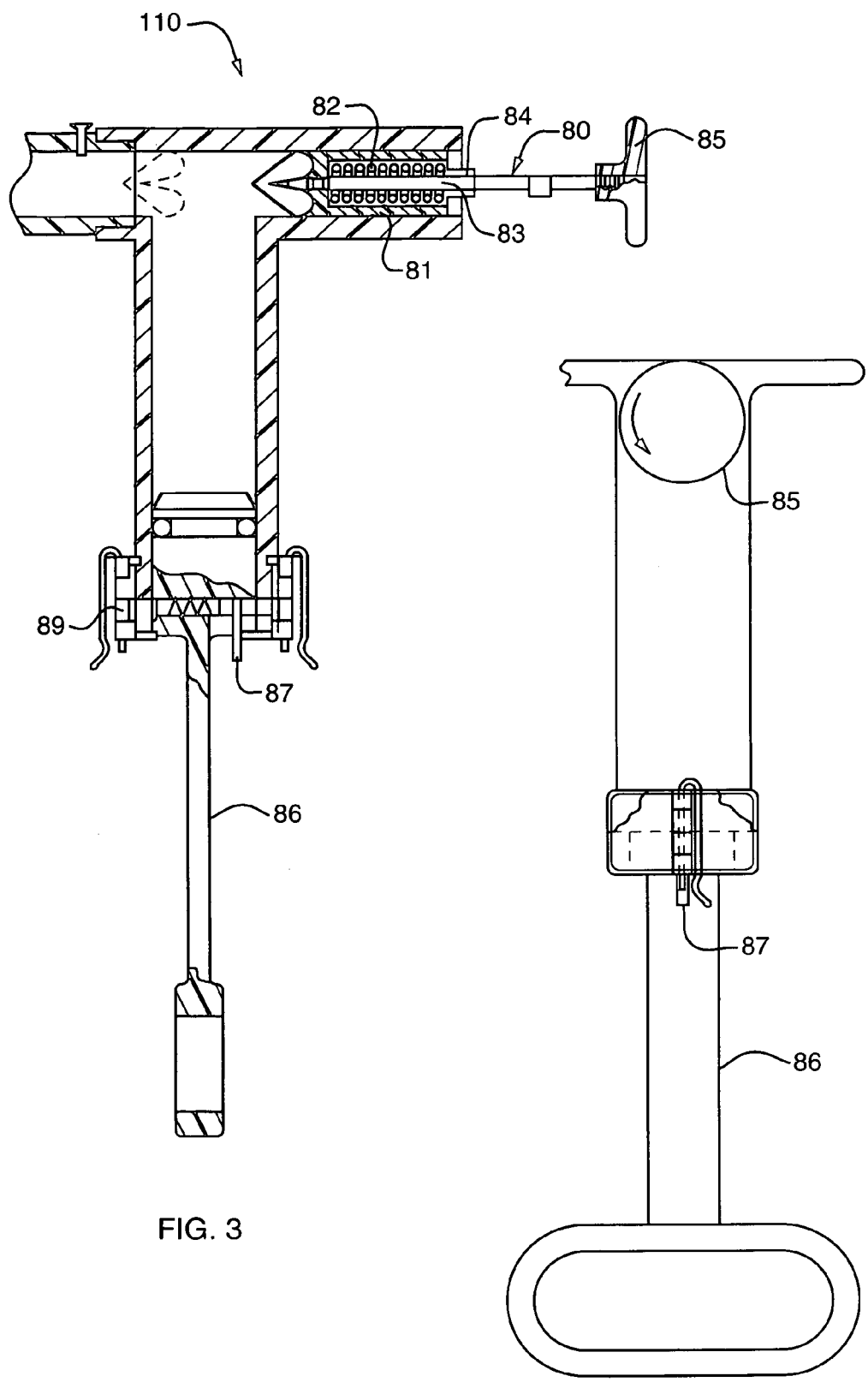
FIG. 3 is a fragmentary schematic view of a third embodiment of the invention.
FIG. 4 is a view in elevation, partly in section, as seen from the right-hand portion of FIG. 3.
Figure 11:
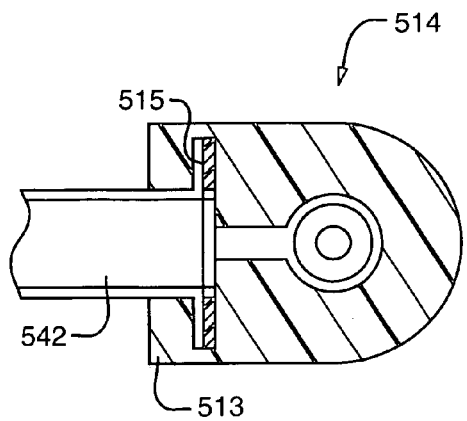
FIG. 11 is a transverse sectional view as seen from the plane 11-11 in FIG. 9.

Turning now to the third embodiment (FIGS. 3 and 4), parts corresponding to those of the first and second embodiments have been designated by similar reference characters with the additional prefix "2".

In the third embodiment, the construction is further simplified for manufacture. The striker element 80 is molded to include a recess 81 for a coil spring 82. A central shaft 83 is threadedly engaged at an inner end. The outer end includes an enlargement 84 and a threaded knob 85 which rotates to maintain the striker in cocked position, thus eliminating the need for a trigger.

The plunger element 86 includes a resiliently urged latch with a release lever 87, and a retaining ring 88 which maintains spring 89 in position, as shown. The entire plunger element may be injection molded.

Turning now to the fourth embodiment of the invention (FIGS. 5 through 8, inclusive), the mouthpiece 90 is provided with a flange 91 at the engagement end thereof with the frangible membrane 92 and seal lying in parallel planes. The barrel 93 is slotted at 94 to receive this structure. The striker is generally similar to that of the third embodiment without a separate trigger.

The vacuum plunger 95 includes a laterally-extending handle 96 riding in a slot 97 in the barrel 98. A latch 99 retains the plunger in vacuum-forming position. When released, a spring 100 moves the plunger to the proximal end of the slot wherein the inner end of the plunger is positioned to block the striker which is maintained in normally cocked position until the vacuum plunger is moved outwardly. Thus, the inner end of the plunger blocks movement of the striker to penetrate the membrane should it be accidentally released.

Turning now to the fifth embodiment of the invention (FIGS. 9-12), this embodiment differs from the above-described embodiments in the elimination of a frangible membrane to provide instantaneous negative pressure, and the striker means for penetrating the membrane. Instead, the first cylindrical element is modified by considerably shortening the length thereof, and incorporating a finger operated valve which contains generated vacuum pressure for instantaneous application to the mouthpiece element. The valve is returned to closed position by the inner end of the vacuum plunger.

Figure 9:
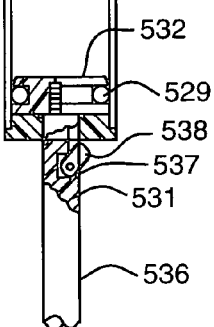
FIG. 9 is a longitudinal sectional view of a fifth embodiment.

Referring to FIG. 9, et. seq., the fifth embodiment, generally indicated by reference character 510 includes a molded housing 511 with a laterally-extending recess 512 accommodating the flanged end 513 of a mouthpiece element 514. The end includes a sealing member 515, but the frangible membrane of the earlier embodiments is eliminated.

Figure 10:
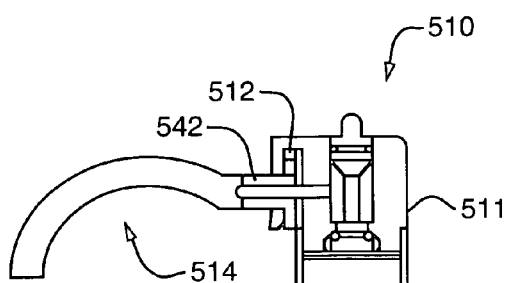
FIG. 10 is a fragmentary enlarged sectional view corresponding to an upper portion of FIG. 9.
Figure 10:
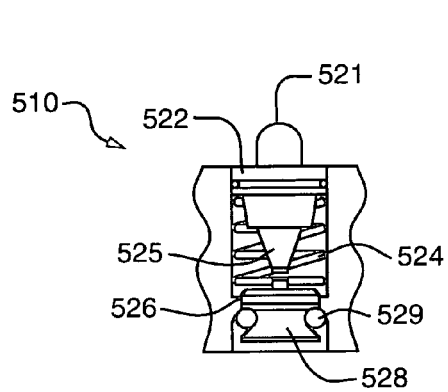
Figure 12:
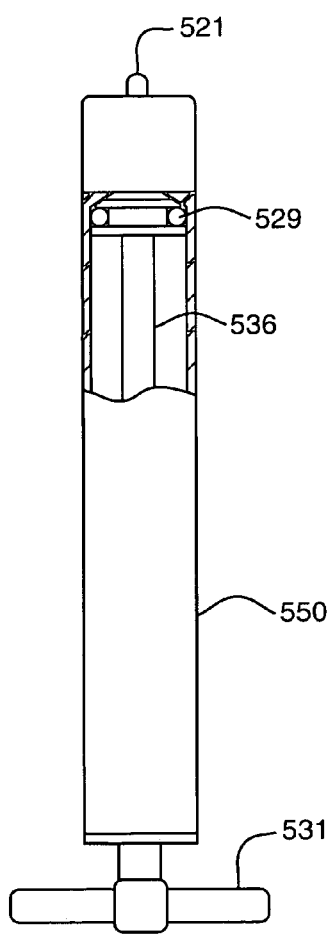
FIG. 12 is a longitudinal sectional view of an alternate form of the fifth embodiment.

Referring to FIG. 10, a valving element 520 includes an elongated push button 521 positioned in a cylindrical channel 522 for reciprocation with a return spring 524. An inner end 525 of the button 521 selectively engages a traversely-extending plate 526 against a sealing member 527, including a main body 28 and an o-ring seal 529.

The sealing member is positioned in a laterally-extending barrel 530, which slidably accommodates a vacuum plunger 531, which includes a planar valve seating member 532, as well as an o-ring seal 529. The vacuum plunger 531 includes a rod 536 having one or more recesses 537 engaged by a locking means 538 as in the earlier-described embodiments. In the alternate form shown in FIG. 9, plural recesses (not shown) may be provided so that the degree of vacuum obtained may be adjusted in accordance with the individual requirements.

Operation of the fifth embodiment will be apparent from a consideration of the drawings. The device will normally be stored with the plunger element within the vacuum chamber, which will result in the valving element 520 being seated in sealed relation by the spring 524 and movement of the plunger 532. When the device is readied for use, the plunger element is pulled outwardly by the user to generate the required level of vacuum, following which the plunger locking mechanism is latched. The mouthpiece element is then positioned within the mouth of victim, following which the button 521 is pressed to dislodge the sealing member 526, whereby vacuum pressure is transmitted through a laterally-extending channel 542 to the mouthpiece element. The sealing member is returned to sealed relation by contact of the inner end of the plunger after use.

We wish to be understood that we do not consider the invention to be limited to the details of structure shown and described in the specification, for obvious modifications will occur to those skilled in the art to which the invention pertains.

We claim:

1. A device for vacuum removal of a lodged mass from the throat of a victim, comprising: a first generally cylindrical tube having first and second ends defining a continuous bore, said first end having means for selectively engaging a mouthpiece element in substantially leak-proof relation; a resilient striker element positioned within said second end of said first tube selectively maintained in relatively cocked position by a manually operable means; a laterally-extending vacuum pump element including a second tubular member having a first end communicating with said first cylindrical tube and a second open end defining a bore, including a recess at a second end of said bore; a plunger slidably positioned in said bore having a manually-engageable handle and latching means at an outer end thereof, a sealing member, and a mouthpiece element selectively engageable in sealed relation with said first end of said first tube, said element including a frangible sealing means selectively penetrated by said striker element upon activation of said manually-operable means.

2. A device for the removal of a lodged mass from the throat of a victim, comprising: a housing having a principal axis, said housing having a laterally-extending member having means for selectively engaging a free end of a mouthpiece element; said laterally-extending member including a laterally-extending channel; said housing having an axially-extending bore communicating with said laterally-extending channel, and manually operable valving means disposed within said bore; an axially-extending barrel, an elongated vacuum plunger slidably positioned within said barrel, and having locking means thereon, said barrel having corresponding locking means thereon for selectively maintaining said plunger in outward, vacuum-generating position; movement of said plunger to an inward position serving to contact said valving means and return it to closed condition.

3. In a device for removing a lodged mass from the throat of a victim, the improvement comprising: a replaceable mouthpiece element, including a tube having a free end closed by a frangible membrane, and a vacuum-generating source having means for engaging said free end in sealed relation, said source including a resilient striker element for penetrating said membrane following positioning of said mouthpiece element; said vacuum source including a manually-operated single stroke vacuum pump plunger, said vacuum pump including latch means for maintaining said plunger in vacuum-creating position.

* * * * *